United States Patent [19]

Peers et al.

[11] Patent Number: 5,837,218

[45] Date of Patent: *Nov. 17, 1998

[54] NON-RECEPTOR CELL MEDIATED IMAGING AGENTS

[75] Inventors: Susan H. Peers; Anne Goodbody; Alfred Pollak; John Thornback, all of Toronto, Canada

[73] Assignee: Resolution Pharmaceuticals Inc., Mississauga, Canada

[ * ] Notice: The term of this patent shall not extend beyond the expiration date of Pat. No. 5,688,489.

[21] Appl. No.: 700,776

[22] Filed: Aug. 22, 1996

Related U.S. Application Data

[62] Division of Ser. No. 529,060, Sep. 15, 1995, Pat. No. 5,688,489.

[51] Int. Cl.⁶ ............................ A61K 51/00; A61M 36/14
[52] U.S. Cl. ........................ 424/1.69; 530/326; 424/1.65; 534/14
[58] Field of Search .................................. 424/1.11, 1.65, 424/1.69, 9.1; 534/10–16; 530/300, 324–330; 206/223, 569, 570

[56] References Cited

U.S. PATENT DOCUMENTS

| | | | |
|---|---|---|---|
| 4,810,777 | 3/1989 | Zasloff | 530/326 |
| 5,043,176 | 8/1991 | Bycroft et al. | 426/335 |
| 5,180,816 | 1/1993 | Dean | 530/404 |
| 5,277,892 | 1/1994 | Rhodes | 424/1.69 |
| 5,447,914 | 9/1995 | Travis et al. | 514/16 |
| 5,585,353 | 12/1996 | Merrifield et al. | 514/12 |
| 5,688,489 | 11/1997 | Peers et al. | 424/1.69 |

FOREIGN PATENT DOCUMENTS 9311783   6/1993   WIPO .

*Primary Examiner*—Gary E. Hollinden
*Assistant Examiner*—Dameron Jones
*Attorney, Agent, or Firm*—Nikaido Marmelstein Murray & Oram LLP

[57] ABSTRACT

Detectably labelled non-receptor mediated cell-associating compounds are provided for use in the diagnostic imaging of target sites in a mammal. Cell-associating compounds may be directly labelled, or labelled via a chelating compound to form a conjugate. Such cell-associating compounds are particularly useful to image target sites such as tumour sites and sites of infection.

17 Claims, 3 Drawing Sheets

NON-RECEPTOR CELL MEDIATED IMAGING AGENTS

This is a divisional, of application Ser. No. 08/529,060 filed Sep. 15, 1995 now U.S. Pat. No. 5,688,489.

FIELD OF THE INVENTION

The present invention relates to imaging. In particular, the present invention relates to non-receptor mediated imaging of a target site.

BACKGROUND OF THE INVENTION

Radiopharmaceuticals have been developed which image a wide range of target sites including, for example, sites of inflammation/infection, tumor and thrombus, among others. The imaging activity of such radiopharmaceuticals is based on a receptor interaction at the target site between the radiopharmaceutical and the target. Receptor-mediated imaging of this type is believed to provide specificity in distinguishing between target and non-target sites due to differential distribution of the receptor.

However, disadvantages have been found to exist with receptor-mediated imaging. For example, due to the existence of endogeneous receptor ligand in vivo, completion between radiolabelled receptor ligand or the active portion of the receptor, i.e. the radiopharmaceutical, and endogenous receptor ligand can result in poor imaging of a given target if a significant quantity of endogenous ligand interacts at receptor sites of the target. A similar problem can occur if the imaging solution contains a significant quantity of unlabelled receptor ligand. Competition between labelled and unlabelled ligand for receptor sites can result in the binding of a high level of unlabelled ligand. Since the number of receptor sites on any given target is fixed, this can again result in poor imaging.

There exists a need, thus, for an effective means to image target sites, which overcomes at least one of the disadvantages of prior imaging means.

SUMMARY OF THE INVENTION

An object of the present invention is to provide a non-receptor based means for imaging a target site.

Thus, in one aspect of the present invention there is provided a detectably labelled non-receptor mediated cell-associating compound. In another aspect of the present invention, a conjugate comprising a non-receptor mediated cell-associating compound linked to a chelator is provided.

Other aspects of the present invention include diagnostic compositions comprising the detectably labelled compound or conjugate defined above, and methods of using such compositions for imaging target sites in a mammal.

In another aspect, there is provided a kit comprising the conjugate; a reducing agent; a transchelating agent; and a buffering agent.

These and other aspects of the present invention will be described by reference to the following figures in which:

DETAILED DESCRIPTION OF THE INVENTION

Figure 1:
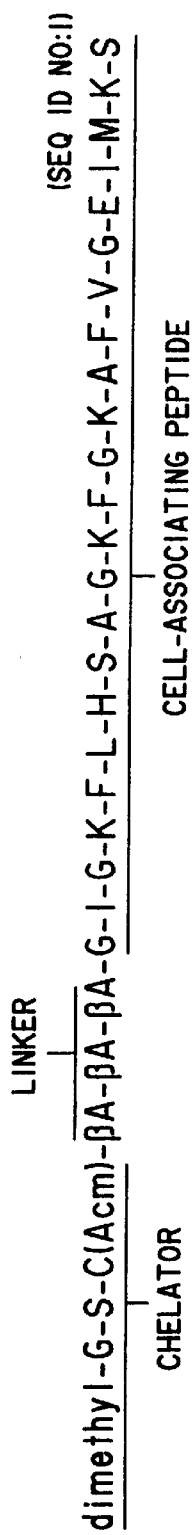
FIG. 1 provides the amino acid sequence (SEQ ID NO:1) of a peptide conjugate in accordance with the present invention.

The present invention provides detectably labelled non-receptor mediated cell-associating compounds useful to image target sites in a mammal.

The term "target site" as it is used herein refers to sites within a mammal comprising abnormal cells, e.g. tumour cells or pathogenic cells, which do not normally exist in the mammalian body or which do not normally exist at the concentration or at the location of the target site. As one of skill in the art will appreciate, pathogenic cells refer to prokaryotic and eukaryotic microorganisms such as bacterial, viruses, fungi and protozoa.

The term "cell-associating compound" is used herein to refer to compounds which recognize and couple with a target cell. In this context, "a non-receptor mediated cell-associating compound" in one which interacts reversibly or irreversibly in a non-receptor-mediated fashion with a target cell to an extent which is statistically significant when compared with background binding to the same target. The term "non-receptor-mediated" refers to an association of the compound with the target cell that does not involve interaction with a specific receptor of the target cell. Such non-receptor mediated cell association can be determined using, for example, a filter separation assay. Using this assay, receptor mediated cell association will be saturably, while non-receptor mediated cell association will not be saturable. In this way, the two types of cell association can readily be differentiated.

In order for the cell-associating compounds of the present invention to function efficiently in their capacity as imaging agents, the native, cell-associating conformation of the compound must be essentially retained when the compound is prepared into the form in which it will be used to image, i.e. labelled and/or conjugated forms. As will be described in detail herein, the cell-associating compounds may be directly labelled or indirectly labelled via a chelator to which the compounds is first conjugated. Thus, on conjugation to a chelator and/or on labelling with a radionuclide metal, secondary structures of the cell-associating compound, such as cross-linkages, α-helical structures and β-sheets, should be retained to least about 50% of their native state, an preferably to at least about 65% of their native state, as determined using, for example, circular dichroism studies.

Examples of non-receptor mediated cell-associating compounds in accordance with the present invention include, but are not limited to, antibiotic peptides such as cecropins, defensins, tachyplesins and magainins (including magainin-1, magainin-2, magainins A–G, and other magainin-related peptides), peptides from hemolymph of insect and lepidoptera larvae and pupae, hemolymph of horseshoe crabs, bee venom, peptides from amphibian skin and gastric secretions, mammalian-related equivalents from mucosal surfaces, gastric and other gastrointestinal secretions or leukocytes, and functionally equivalent analogues derived from one of the aforementioned non-receptor mediated cell-associating compound or any other suitable cell-associating compound. Preferred cell-associating compounds are microorganism-binding peptides, and more preferably, peptides which exhibit antibiotic activity. Other preferred compounds in accordance with the present invention are peptides comprising at least a portion of α-helical structure. Peptides of the magainin family, and functional equivalents thereof, thus, are particularly preferred compounds for imaging as set out herein.

Functionally equivalent analogues of a non-receptor mediated cell-associating compound are suitable for imaging target sites, and include derivatives of a given cell-associating compound which function in essentially the same manner as the underivatized form thereof. Examples of such functionally equivalent analogous include, but are not limited to, analogous comprising N- or C-terminal modifications which function to protect the termini from undesirable attack. By "undesirable attack" is meant any type of enzymatic, chemical or biochemical breakdown of the compound at its termini which is likely to affect the function of the compound to image target sites, N- and C-terminal modification of peptides is common practice in the art in the preparation of peptides having greater stability, particularly for in vivo use. Such modifications include the addition of protecting groups such as the protecting groups used conventionally in the art of organic synthesis. Suitable N-terminal protecting groups include, for example, lower alkanoyl groups of the formula R—C(O)— in which R is a linear or branched lower alkyl chain comprising from 1–5 carbon atoms. A preferred group for protecting the N-terminal end of the present compounds is the acetyl group, $CH_3C(O)$. Other groups useful to protect the N-terminus end from undesired attack are amino acid analogous lacking the α-amino function. Suitable C-terminal protecting groups include groups which form ketones or amides at the carbon atom of the C-terminal carboxyl, or groups which form esters at the oxygen atom of the carboxyl. Ketone and ester-forming groups include alkyl groups, particularly branched or unbranched lower alkyl groups comprising from 1 to 5 carbon atoms, e.g. methyl, ethyl and propyl groups, while amide-forming groups include amino functions such as primary amines (—NH2), or alkylamino functions, e.g. monoalkylamino and dialkylamino groups such as methylamino, ethylamino, dimethylamino, diethylamino, methylethylamino and the like. Amino acid analogues are also suitable for protecting the C-terminal end of the present compounds, for example, decarboxylated amino acid analogues such as agmatine. Of course, N- and C-protecting groups of even greater structural complexity may alternatively be incorporated to protect the N- and C-terminal ends of the compound from attack provided that the cell-associating activity of the compound is not adversely affected by the incorporation thereof.

Functionally equivalent analogues also include compounds which incorporate amino acid substitution, deletion or addition which does not adversely affect the activity of the compound to associate with its target. For example, one or more of the amino acids in the compound, which naturally occur in the L-form, may be substituted by the D-form thereof. Alternatively, one or more of the amino acids may be derivatized at the side-chain moiety, or may be replaced altogether by a different amino acid. For example, derivatization of sidechain moieties may be necessary to avoid oxidative damage, i.e. damage which may occur to the peptide on exposure to the radionuclide labelling agent or other agents associated with the labelling procedure. Cross-bridges, such as disulfide linkages, are particularly sensitive to such oxidative damage and can be replaced with an amide-containing bridge. In another example, due to the importance of retaining the compound's native secondary structure, it may be desirable to replace residues within the compound which do not contribute to the stability of the compound's conformation with residues which enhance conformational stability. Thus, residues in a compound's α-helical structure which have a low helical propensity may be replaced by residues having a greater helical propensity. In the case of the magainin peptide, for example, each of the serine at position 8, the glycine at position 13 and the glycine at position 18 have a low helical propensity. Accordingly, it may be desirable to replace such residues with residues having a greater propensity such as alanine residues.

Alternatively, a functionally equivalent analogue may be synthetically derived from one or more suitable compounds, optionally comprising regions from compounds which are not cell-associating. In this way, desirable features from each compound can be incorporated into one hybrid compound. Thus, a suitable synthetically derived analogue in accordance with the present invention may comprise only the cell-associating region of a compound, alone or in conjunction with a region from another unrelated compound.

Cell-associating compounds of the present invention can be peptides. Such peptide compounds, including functional equivalents thereof, can be readily prepared by standard, well-established techniques of solid-phase peptide synthesis (SPPS) as described by Stewart et al. in *Solid Phase Peptide Synthesis,* 2nd Edition, 1984, Pierce-Chemical Company, Rockfor, Ill.; and as described by Bodanszky and Bodanszky in *The Practice of Peptide Synthesis,* 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which do not affect the final peptide product. Stepwise synthesis of the peptide is carried out by the removal of the N-protecting group from the initial amino acid, and coupling thereto of the carboxyl end of the next amino acid in the sequence of the oligopeptide. This amino acid is also suitably protected. The carboxyl of the incoming amino acid can be activated to react with the N-terminus of the bound amino acid by formation into a reactive group such as formation into a carbodiimide, a symmetric acid anhydride or an "active ester" group such as hydroxybenzotriazole or pentafluorophenyl esters. The preferred solid phase peptide synthesis methods include the BOC method which utilizes tert-butyloxycarbonyl as the α-amino protecting group, and the FMOC method which utilizes 9-fluorenylmethloxycarbonyl to protect the α-amino of the amino acid residues, both methods of which are well-known by those of skill in the art.

Recombinant technology can also be used to prepare peptide cell-associating compounds of the present invention. This generally entails expression from a genetically engineered cellular source having incorporated expressibly therein a heteromeric DNA molecule coding for the desired peptide. Recombinant DNA expression systems, culturing media and culturing protocols enabling production in various host organisms is established in the art, and these systems can be employed in the conventional manner for the specific purpose of producing the desired compound. The compound is produced by culturing the cellular host in which the heterologous DNA is expressibly incorporated. Upon expression, the product is then recovered, using standard methods of recovery, from the culture broth for purification.

To obtain DNA coding for the peptide, a variety of established techniques may be applied. For example, DNA coding for the desired compound may be isolated as cDNA from commercially available human cDNA libraries. A more expeditious method, however, to arrive at the desired DNA may be de novo synthesis in accordance with methods standard in the gene synthesis art which involve the successive 3' to 5' coupling of suitably protected nucleotide reagents in an automated DNA synthesizer, followed by recovery using gel purification of the deprotected polynucleotide. The block ligation approach may be employed whereby "blocks" of oligonucleotide pairs of up to about 80 nucleotides in length are prepared and ligated in correct succession by overhang complementarity, as described for example by Wosnick et al in Gene, 1989, 76:153. This "block" approach is particularly useful in the synthesis of oligonucleotides which are greater than about 100 nucleotides in length. Alternatively, the desired DNA may be synthesized in toto, and them amplified by polymerase chain reaction (PCR), using the approach described by Barnett et al. in Nucl. Acids Res., 1990, 18(10):3094.

The desired cell-associating compound can also be obtained by isolation from natural sources using well-established methods in the art. For example, many of the cell-associating compounds suitable for imaging in accordance with the present invention originate from amphibian or insect sources, and can be readily obtained form such sources. A number of other suitable compounds represent mammalian counterpart compounds and, thus, can be isolated from readily available mammalian sources.

The peptide compound should be purified once it has been isolated or synthesized by either chemical or recombinant techniques. For purification purposes, there are many standard methods that may be employed including reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can also be used to separate peptides based on their charge.

In order to ensure that the peptide obtained using any of the techniques described above is the desired peptide for use in compositions of the present invention, analysis of the peptide composition is carried out. Such composition analysis may be conducted using high resolution mass spectrometry to determine the molecular weight of the peptide. Alternatively, the amino acid content of the peptide can be confirmed by hydrolyzing the peptide in aqueous acid, and separating, identifying and quantifying the components of the mixture using HPLC, or an amino acid analyzer. Protein sequenators, which sequentially degrade the peptide and identify the amino acids in order, may also be used to determine definitely the sequence of the peptide.

Once prepared, the selected cell-associating compound, or functional equivalent thereof, is detectably labelled, i.e. labelled such that the compound can be detected in vivo by any of a number of accepted techniques in the art of diagnostic imaging. There are a number of radionuclide metals that can be used to label detectably the present compounds in accordance with the present invention. These include both gamma-emitters and positron-emitters. Examples of such radionuclides include, but are not limited to, fluorine-18, copper-64, copper-65, gallium-67, gallium-68, bromine-77, ruthenium-95, ruthenium-97, ruthenium-103, ruthenium-105, technetium-99m($^{99m}$Tc), mercury-107, mercury-203, iodine-123, iodine-125, iodine-126, iodine-131, iodine-133, indium-111, indium-113m, rhenium-99m, rhenium-105, rhenium-101, rhenium-186 and rhenium-188, tellurium-121m, tellurium-122m, tellurium-125m, thulium-165, thulium-167, thulium-168 and nitride or oxide forms derived therefrom. Although standard scintigraphic techniques are primarily used in the detection of the radioactivity emitted by radionuclides, the instrumentation used for this purpose may vary depending on the radionuclide used and on the nature of the target being imaged. The gamma camera and the rectilinear scanner each represent instruments useful to detect radioactivity in a single plane. SPECT (Single Photon Emission Computed Tomography) and PET (Positron Emission Tomography) devices represent instruments that are capable of detecting radioactivity in more than one dimension.

The most preferred radionuclide for use in detectably labelling compounds in accordance with the invention is $^{99m}$TC. This radionuclide exhibits a number of desirable characteristics including a desirable half-life of about 6 hours which allows for rapid imaging on injection. It is also relatively safe allowing the injection of a dose of more than 30 mCi with low radiation exposure to the patient. Finally, it is conveniently available from $^{99}$Mo-$^{99m}$Tc generators.

In the use of radionuclides such as $^{99m}$Tc, a metal chelator compound is required to link the metal to the cell-associating compound to be labelled to form a conjugate. In this regard, it will be appreciated that such a conjugate can initially be prepared which will then be labelled with the radionuclide metal, or in an alternative approach, a metal-labelled chelator can be prepared for subsequent linkage to the selected cell-associating compound.

For diagnostic imaging purposes, a chelator is a compound which has a reactive functional group for labelling by a radionuclide and, on binding to a radionuclide metal, forms a complex that is stable under physiological conditions. Many chelator compounds have been developed for this purpose. Commonly used chelating agents include, for example, DTPA (diethylenetriaminepentaacetic acid) and ethylene diamine tetracetic acid (EDTA). Other chelators appropriate to link a radionuclide metal label to a compound in accordance with the present invention are described in standard texts such as *Advanced Inorganic Chemistry*, 4th edition, 1980, F. A. Cotton and G. Wilkinson, John Wiley & Sons. However, as will be appreciated by those of skill in the art, the most suitable metal chelating agent will vary with the metal to be chelated, e.g. depending on its particular coordination.

Chelators suitable specifically for linking $^{99m}$Tc to cell-associating compounds in accordance with the present invention typically present, as a metal coordinating configuration, a combination of four nitrogen and sulfur metal-coordinating atoms. Examples include compounds having $N_4$, $N_3S$ and $N_2S_2$ conformations. However, such chelators may incorporate other metal-coordinating atoms including oxygen, phosphorous and selenium. In one embodiment of the present invention, $N_3S$ chelators, such as those described in co-pending U.S. application Ser. Nos. 08/171,737, 08/279,155 and 08/299,636, the contents of each of which are incorporated herein by reference, are used to prepare the present conjugates. In another embodiment, $N_2S_2$ chelators, such as those described in co-pending U.S. application Ser. No. 08/116,504, also incorporated herein by reference, are used to prepare the present conjugates. In a specific embodiment of the present invention, and as set out in the specific examples herein, one chelator used to prepare peptide conjugates is dimethyl-glycine-serine-cysteine (Acm). Reference can be made to FIG. 1 for the amino acid sequence of a specific conjugate which incorporates this chelator.

A conjugate can be formed by reacting the N-terminal residue of the cell-associating compound with an appropriate functional group of the chelator such as a carboxyl group or activated ester. For example, a conjugate in accordance with the present invention may incorporate the chelator, EDTA, via a linkage between the carboxyl substituent on the ethylene chain of EDTA with the N-terminal residue of the selected compound. Synthesis of EDTA derivatives of this type are described in Arya et al, (Bioconjugate Chemistry 1991, 2:323) in which the four coordinating carboxyl groups of EDTA are each blocked with a t-butyl group while the carboxyl substituent on the ethylene chain is left free to react with the amino group of the peptide to form the desired conjugate.

Desirably, the conjugate incorporates a chelator which is peptidic in nature. This allows for the preparation of an intact conjugate using either synthetic or recombinant techniques when the cell-associating compound is also a peptide. For example, continuous synthesis of the cell-associating compound and chelator compound can be conducted using solid-phase peptide synthesis. Thus, the compound and chelator can be synthesized in toto starting from the C-terminal residue of the peptide and ending with the N-terminal residue of the chelator. This type of in toto synthesis is described in detail in the specific examples for the synthesis of a magainin conjugate and a cecropin-melittin conjugate in accordance with the present invention. Alternatively, if recombinant techniques for preparing the conjugate are preferred, DNA encoding the conjugate in toto can be prepared using the de novo synthesis described above, and the DNA can then be incorporated into a cellular source for expression.

Conjugates may further incorporate a linking group that serves to couple the cell-associating compound to the chelator while not adversely affecting either the targeting function of the compound or the metal binding function of the chelator. Such linking groups are useful to space the chelator from the cell-associating compound to ensure that the chelator does not interfere with the targeting function of the cell-associating compound. Suitable linking groups include peptide chains and alkyl chains modified to include reactive groups for coupling to both the compound and the chelator. In one embodiment, the linking group is a peptide of 1–5 amino acid residues and more particularly, 1–3 residues. Preferred linking groups include -Gly- and -Gly-Asp-Gly-, as well as chains of synthetic amino acid residues including, for example, chains of 1 or more -βAla- residues. A peptide chain is the preferred linking group when the selected cell-associating compound and chelator are also peptidic in nature. In this way, the conjugate can be synthesized in toto, as described above, using solid- or solution-phase techniques.

In another embodiment, the linking group is an alkyl chain incorporated into the conjugate by reacting the N-terminal amino group of the cell-associating compound with a first functional group on the alkyl chain such as a carboxyl group or an activated ester. Subsequently the chelator is attached to the alkyl chain to complete the formation of the conjugate by reacting a second functional group on the alkyl chain with an appropriate group on the chelator. The second functional group on the alkyl chain is selected from substituents that are reactive with a functional group on the chelator and preferably not reactive with the N-terminal residue of the compound. For example, when the chelator incorporates a functional group such as a carboxyl group or an activated ester, the second functional group of the alkyl chain linking group is desirably an amino group. It will be appreciated that formation of the conjugate may require protection and deprotection of the functional groups present in order to avoid formation of undesired products. The use of such protection and deprotection techniques is described above.

To be suitable for use in diagnostic compositions of the present invention, the cell-associating compound or conjugate must be of "pharmaceutical grade" purity so as to be suitable for administration to a mammal for the purpose of imaging target sites. Accordingly, the cell-associating compound must exhibit a uniform and authentic composition, for example a uniform and authentic amino acid composition in the case of a peptide, and must not include extraneous material. Furthermore, the compound must meet the criteria as set out by national pharmaceutical regulatory bodies.

Labelling of a cell-associating compound or conjugate can be achieved by various methods common in the art of coordination chemistry. The radionuclide is, in some cases, incorporated directly within the compound. Such direct labelling would be conducted when using radioisotopes of iodine or indium. In this regard, the chloramine-T reaction is the standard reaction used to label a selected compound with iodine, while a reaction utilizing DTPA is generally used to label a selected compound with indium. In the case of labelling a conjugate, it will be appreciated by those of skill in the art that the conjugate can be prepared and subsequently labelled with a metal radionuclide; however, in an acceptable alternative, the chelator itself can be labelled with the selected metal radionuclide and subsequently coupled to the cell-associating compound to form the labelled conjugate, a process referred to as the "prelabelled ligand" method.

In a specific embodiment, the following general procedure is used to label the selected conjugate with the radionuclide, technetium-99m. A conjugate solution is prepared by dissolving the conjugate in an aqueous alcohol such as ethanol. The solution is degassed to remove oxygen. Protecting groups on the metal complexing atoms of the conjugate's chelator are removed with a suitable reagent. In the labelling step, sodium pertechnetate is added to the conjugate solution with a sufficient amount of a reducing agent such as stannous chloride to reduce the pertechnetate, and the solution is heated. The resulting labelled conjugate is then isolated from the reaction mixture, for example, chromatographically.

In an alternative method, the conjugate can be labelled using a transchelation reaction. The technetium source is a solution of technetium complexed with labile ligands which facilitate ligand exchange with the conjugate. Suitable such labile ligands for transchelation include tartarate, citrate and glucoheptonate.

Another approach for labelling conjugates of the present invention is described in co-pending U.S. application Ser. No. 08/152,680, the contents of which are incorporated herein by reference. Briefly, the conjugates are immobilized on a solid-phase support via a linkage formed between the support and one of the chelator metal complexing atoms. Cleavage of the conjugate, thus, is attained on elution with a metal labelling agent to yield a labelled conjugate. Preferably, a complexing sulfur atom is coupled to the support which is functionalized with a sulfur protecting group such as maleimide.

Diagnostic composition comprising a detectably labelled cell-associating compound or a conjugate in accordance with the present invention are prepared for use in imaging potential target sites in a mammal, including for example tumour sites and sites of infection. As used herein, the term "infection" refers to the invasion and multiplication of microorganisms, including bacteria, viruses, fungi, protozoa and other microorganisms, in host body tissues. The term "mammal" as it is used herein is meant to encompass humans, domestic animals such as cats, dogs and horses, livestock such as cattle, pigs, goats, and sheep, and non-domesticated mammals.

The diagnostic compositions comprise a diagnostically effective amount of a detectably labelled cell-associating compound together with a pharmaceutically acceptable carrier. In this context, the term "pharmaceutically acceptable" means acceptable for use in the pharmaceutical and veterinary arts, i.e. a carrier which is non-toxic and which does not adversely affect the activity of the compound in its function to image target sites. The term "diagnostically effective amount" means an amount of the labelled cell-associating compound or conjugate sufficient to allow detection of a target site when compared to background signal. In this regard, a "region of interest" (ROI) ratio can be used to determine the efficiency of a labelled compound to image target sites. For the purposes of the present invention, an ROI ratio is the ratio of counts of radioactivity obtained, on administration of a labelled compound in accordance with the present invention, between a target site, such as a site of infection, and a control site, such as a non-infected site which may or may not be inflamed. An ROI ratio of greater than 1, and preferably greater than 2, indicates a specificity of the labelled compound for the target site. Desirably, the ROI ratio of a given labelled compound in accordance with the present invention is at least 5, and most preferably, the ROI ratio is at least 10. Based on the efficiency of the labelled compound to image a target site, i.e. based on the ROI ratio, as determined using suitable models such as the rat animal model described in the specific examples herein, diagnostically effective amounts can then be determined.

Pharmaceutically acceptable carriers useful to prepare compositions for in vivo administration include conventional carriers used in formulating peptide-based drugs, such as diluents, excipients and the like. Reference may be made to "Remington's Pharmaceutical Sciences", 17th Ed., Mack Publishing Company, Easton, Pa., 1985, for guidance on drug formulations generally. As will be appreciated, the pharmaceutical carriers used to prepare compositions in accordance with the present invention will depend on the administrable form to be used in the diagnosis of an afflicted mammal.

According to one embodiment of the invention, the detectably labelled compounds are formulated for administration by intravenous injection and are accordingly provided as aqueous solutions in sterile and pyrogen-free form and optionally buffered or made isotonic. Thus, the compounds may be administered in distilled water or, more desirably, in saline or 5% dextrose solution. Water solubility of the present compounds may be enhanced, if desired, by incorporating into the composition a solubility enhancer, such as cetyltrimethylammonium bromide or chloride, or by preparing the acid addition salt thereof. Lyoprotectants, such as mannitol, sucrose or lactose and buffer systems, such as acetate, citrate and phosphate are other components that may be included in the formulation, as may bulking agents such as serum albumin. Stabilizers to prevent or minimize radiolytic damage may also be added to the formulation and include such compounds as ascorbic acid, gentisic acid, or other appropriate antioxidants.

For use in diagnosis, precise dosage sizes of the compound or conjugate are established in appropriately controlled clinical trials, and will correspond to an amount of detectably labelled cell-associating compound sufficient to detect the tissue of a target site as compared to the background signal obtained in normal tissue, without causing intolerable side effects and without unacceptable exposure to radioactivity. It is anticipated that an effective regimen for diagnosis will involve the intravenous administration of dosages in the range of 1 mCi–100 mCi per 70 kg (the average weight of a human). It will be appreciated, however, that the exact dosage sizes required to attain the desired diagnostic effect will vary according to the specific individual being treated, i.e. age, sex and general health, and the radionuclide metal used as the label. In this regard, it is noted that dosages in the range of 5 mCi–40 mCi per 70 kg are typical of technetium-labelled diagnostics.

In a specific embodiment of the present invention, the labelled cell-associating compound identified in FIG. 1 was used to diagnose specifically a site of infection versus a site of inflammation not related to infection. As set out above, the term "infection" includes within its scope bodily invasion by bacterial, viruses, fungi, protozoa and other microorganisms. The term "inflammation", on the other hand, refers to the protective response elicited by injury which may be caused by any one of infectious microorganisms, autoimmune processes, extreme temperature, electrical or chemical stimuli or mechanical trauma, for example. As set out in the specific examples, the labelled peptide of FIG. 1 was found to bind to various microbial cells. Thus, an in vivo experiment was conducted in which animals having either a site of infection or a site of non-infectious inflammation were injected with the labelled cell-associating compound of FIG. 1. At appropriate time intervals following injection, accumulated radioactivity at each of these sites was determined. The results of this experiment demonstrate that the peptide is useful in a diagnostic sense to image specifically sites of infection versus sites of non-infectious inflammation. This labelled peptide was also found to bind tumour cells further indicating its use in the diagnosis and/or treatment of tumour-related conditions.

In another aspect of the present invention, a kit is provided comprising a conjugate; a reducing agent; a buffering agent; and a transchelating agent. The kit provides all the components required to prepare a detectably labelled compound for diagnostic use in accordance with the present invention, with the exception of the detectable label which is desirably generated at the clinical site. The components of the kit can be provided in powder form that is readily prepared into an injectable solution on reconstitution with an aqueous solvent as described above. This solution can then be admixed with an appropriate amount of detectable label, i.e. radionuclide metal appropriate for the imaging technique to be employed, and immediately used to image a target site.

Embodiments of the present invention are further described by reference to the following specific examples which are not to be construed as limiting.

EXAMPLE 1

Synthesis of a Conjugate

The conjugate, the amino acid sequence of which is illustrated in FIG. 1, was prepared using classic 9-fluorenylmethyloxycarbonyl (FMOC) synthesis. In this case, an FMOC-serine preloaded 2-methoxyl-4-alkoxyl-benzyl alcohol resin is used on an Applied Biosystems 433A peptide synthesizer.

Cleavage of the resin-peptide from the column, and subsequently, the peptide from the resin were conducted using standard techniques such as those described in Example 5 for the synthesis of the peptide conjugate of FIG. 2. Isolation and purification of the conjugate were also conducted using standard techniques such as those described in Example 5.

EXAMPLE 2

Labelling of a Conjugate with $^{99m}Tc$

The conjugate described in Example 1 was labelled using a transchelation reaction with gluconate being used as the transchelating agent as follows.

A solution (solution A) of the conjugate is prepared in saline (2 mg/mL). 200 uL of the solution is injected into a 3 mL vacutainer. To an empty 3 mL vacutainer with septa is added 1 mL of sodium gluconate (10 mg/mL). 20 uL of stannous chloride solution (20 mg/mL) is injected directly into the gluconate, and this solution (solution B) is shaken gently to mix. Solution C is sodium Tc 99m-pertechnetate obtained from Mallinckrodt in 100 uL of saline.

The vacutainer containing solution A is placed in a specially made lead pot with small holes for ventilation. To solution A is added solution C and then 100 uL of solution B. 20 uL of 0.1M sodium hydroxide is added to the A/B/C mixture to adjust the pH for optimal labelling, followed by brief gentle swirling to mix. At this point the reaction volume is 400 uL. The reaction mixture is heated in a boiling water bath for 10 minutes and then cooled at room temperature for about 1 minute.

HPLC was used to purify the labelled conjugate. Purity is measured as the % are of the labelled conjugate's radiomatic peak relative to 100% of the total activity detected. Colloid formation is not taken into account in the analysis.

A Beckman HPLC system was used with System Gold Software, 112 solvent pumps, a 171 radioisotope detector with a modified† 300 uL solid scintillator cartridge and a 50 uL injection loop. The column used was a Vydac Protein and Peptide C18 reverse phase column. The solvent systems used were acetonitrile with 0.1% TFA (solvent A) and water with 0.1% TFA (solvent B). The column was equilibrated with 100% solvent B and on injection of the labelled conjugate, the solvent ramp was set at 0–100% A over 25 minutes at a flow rate of 2 mL/min. At approximately 40–50% acetonitrile, the conjugate eluted.

†Due to binding to the Ytrium silicate solid scintillant by Tc-glucoheptonate, the column had to be modified. This was achieved by by-passing contact between the HPLC eluent and the scintillant with clear plastic tubing. This modified scintillation cartridge gives a linear response between 1000–10,000,000 DPM, making it suitable for measuring labelling purity.

EXAMPLE 3

Binding Studies of a Labelled Conjugate

The binding activity of the labelled conjugate of FIG. 1 was analyzed against three types of microorganisms, namely S. aureus (ATCC 25923), E. coli (ATCC 25922) and C. albicans (ATCC 14053). On the day before the experiment, S. aureus and E. coli were incubated in 20 ml of tryptic soy broth (Difco) at 37° C. overnight, and C. albicans was incubated in YM broth (Difco) at 30° C. overnight.

The microorganism suspensions were each removed from the incubators, and the optical densities of each suspension was determined. Based on the optical density readings, a volume sufficient to yield absorbances of 0.85 for S. aureus and E. coli suspensions and 3.75 for C. albicans and 600 nm was removed from each suspension and used to inoculate fresh cultures to a final volume of 10 ml.

HL60 tumour cells (ATCC #CCL 240) were grown over several days. On the day of the experiment, the cell suspension was placed in conical centrifuging tubes and centrifuged at approximately 1200 rpm for 15 minutes. The supernatant was discarded and the pellet was washed in 1 ml HBSS (Hank's Balanced Salt Solution from Gibco) with phenol red (Gibco BRL). Each tube was rinsed with an additional milliliter of HBSS, and then the wash HBSS was combined with enough HBSS to make 10 mls. This suspension was spun, washed and respun as described above.

Following the third spin, 3 ml of HBSS was used to resuspend the pellet. Ten Microliters of the HL60 suspension was added to 990 µl of cell counting solution (1% acetic acid in crystal violet). A haemocytometer was used to determine the number of cells per ml in the 3 ml HL60 suspension. An aliquot of the HL60 cell suspension containing $10 \times 10^6$ cells was then transferred to a 10 ml Erlenmeyer flask containing a volume of HBSS that yielded a final volume of 10 ml.

The radioactivity of 20 µl of solution containing the labelled peptide conjugate of FIG. 1 (prepared as described in Example 2 above and used in the HPLC-eluted form) was determined using a Cobra II Auto-Gamma Counter (Canberra Packard), and the volume of solution required to yield $10^6$ counts per minute was then calculated. The calculated volume of peptide solution (20 µl) was aliquoted into the flasks containing each of the innoculated cultures and the HL60 cell suspension, and the flasks were mixed by gentle pipetting and flask swirling.

The flasks were placed in a New Brunswick Reciprocal Water Bath Shaker (Moldel R76) set at 37° C. and a shaking speed of 2.9. Triplicate samples (of 200 µl each) were taken from each flask at 0, 30, 60, 120 and 240 minutes. The samples were filtered on Millipore filters (GSWP 025 00). Filtering was done using a Millipore 1225 Sampling Manifold (XX27 025 50). The filters were washed using 1 ml 0.9% sodium chloride. The vacuum was maintained for approximately 30 seconds prior to the removal of the filters. The collected filters were placed in test tubes for counting on the gamma counter. The pipette tips used to collect the samples were also collected for counting in the same manner as the liquid samples.

The results of this experiment are tabulated below, expressed as a percentage of the counts per minute of an unfiltered sample with background substracted. As can be seen, there is binding of the labelled peptide conjugate to the microorganisms and tumour cells tested.

| Time Elapsed | S. aureus | E. coli | C. albicans | HL60 |
|---|---|---|---|---|
| | Experiment #1 | | | |
| 00:00 | 15.0% | 7.1% | 13.4% | |
| 00:30 | 23.1% | 15.1% | 15.2% | |
| 01:00 | 20.3% | 10.9% | 2.1% | |
| 02:00 | 21.9% | 28.4% | 0.0% | |
| 04:00 | 24.6% | 26.5% | 4.6% | |
| | Experiment #2 | | | |
| 00:00 | 17.8% | 0.0% | 7.7% | 0.0% |
| 00:30 | 41.8% | 12.9% | 15.7% | 5.9% |
| 01:00 | 34.7% | 18.4% | 8.3% | 16.0% |
| 02:00 | 32.9% | 18.1% | 9.7% | 18.6% |
| 04:00 | 29.7% | 14.2% | 26.5% | 31.0% |

EXAMPLE 4

Imaging of an Infected Site

Male Sprague-Dawley rats, weighing 250–350 g, were supplied by Charles River, Canada. They were acclimatised for at least two days prior to use, and maintained under standard conditions with a 12 h light-dark cycle and food and water ad lib.

Infectious agents, E. coli (ATCC 25922) and S. aureus (ATCC 25923) were grown overnight in Tryptic Soy broth (TSB) and agent, C. albicans (ATCC 14053) was grown overnight in YM, each to an optical density representing a concentration of between $10^8$–$10^9$ CFU/ml, as determined by growth curves. The microorganisms were then each diluted, in the appropriate medium as set out above, to a concentration of $10^8$ CFU per 0.2 ml.

Non-infectious inflammation-causing agents were prepared as follows. Carrageenan was prepared by adding λ-carrageenan (Sigma C3889) (200 mg per 10 ml) to warmed, stirred saline. Stirring was continued until a homogenous suspension was obtained. Zymosan A (Sigma Z4250) was suspended in saline at a concentration of 100 mg/ml by vortex mixing.

The rats were anaesthetised using sodium pentobarbitone (Somnotol, 30 mg/kg) i.p. Each rat was injected i.m. into the right thigh with a single infectious or inflammation-causing agent in an amount as indicated below:

E. coli 0.2 ml TSB containing $10^8$ CFU

S. aureus 0.2 ml TSB containing $10^8$ CFU

C. albicans 0.2 ml TSB containing $10^8$ CFU

Zymosan 0.2 ml saline containing 20 mg

Carrageenan 0.2 ml of 2% carrageenan in saline (4 mg)

These doses of infectious or non-infectious agent were chosen on the basis of previously performed experiments which quantified the resulting inflammatory response on the basis of weight of tissue (representing oedema) and MPO content (reflecting neutrophil infiltration). The indicated doses gave equivalent inflammatory responses.

Following the injection, the rats were returned to their cages. Imaging was performed 24 h later. Just prior to imaging, the rats were first anaesthetised with sodium pentobarbitone as described above. 370 MBq (100 μCi) $^{99m}$Tc-peptide conjugate (FIG. 1), prepared as described in Example 2 and used in non-HPLC eluted form, was injected i.v. via the tail vein. At time 0, 30 minutes, 1 hour, 2 hours and 4 hours following injection of the labelled peptide, static images were acquired over 5 min using a Siemens LFOV Digitrac gamma camera set up with a high resolution collimator. Regions of Interest (RIOs) were drawn around the inflamed leg and the control non-injected leg using Siemens MicroDelta 7.2 software. Care was taken to ensure that the ROI's were within 7.5% of the same area, and ROI ratios were calculated using total pixels.

The following results were obtained:

of the ROI ratios of infected v. inflamed sites for each of the experiments (#1 and #2) were calculated for the 1 hour readings. The ratio of the ROI ratios of an E. coli infected site vs. a zymosan inflamed site was 2.22 (Expt.#1), while the ratio of the ROI ratios of an E. coli infected site vs. a zymosan inflamed site was 1.24 (Expt.#2) and vs. a carrageenan inflamed site was 1.34 (Expt.#2). The ratio of the ROI ratio of an S. aureus infected site vs. a zymosan inflamed site was 1.79 (Expt.#1), while the ratio of ROI ratios between an S. aureus infected site vs. a zymosan inflamed site was 2.19 (Expt.#2) and vs. a carrageenan inflamed site was 2.38 (Expt.#2). The ratio between the ROI ratios of a C. albicans infected site vs. a zymosan inflamed site was 2.08.

As can be seen, the ratio of the inflamed site ROI ratio v. the infected site ROI ratio in each case was greater than 1, and in a number of cases, was greater than 2. These results indicate that the compound of FIG. 1 has a specificity for a target site of infection as opposed to the general sites of inflammation caused by the zymosan and carrageenan agents.

EXAMPLE 5

Synthesis of a Synthetic Conjugate

Figure 2:
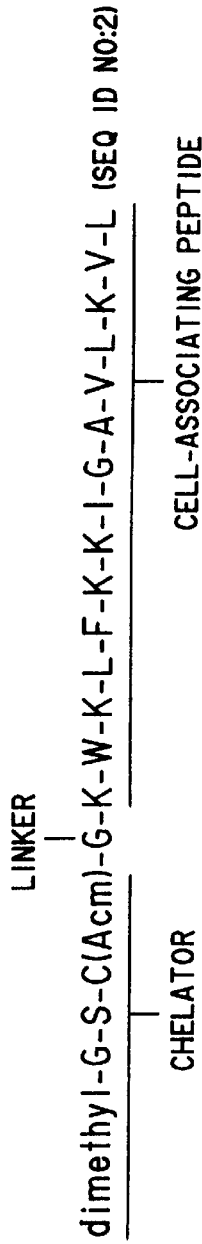
FIG. 2 provides the amino acid sequence (SEQ ID NO:2) of a synthetic peptide conjugate.

The peptide conjugate of FIG. 2 was synthesized on a 0.25 mmol scale using FMOC chemistry with an FMOC-leucine preloaded 2-methoxy-4-alkoxyl-benzyl alcohol resin on an Applied Biosystems 433A peptide synthesizer. The dimethyl-protected glycine and the Acm-protected cysteine residues at the N-terminus of the peptide conjugate (i.e. the chelator portion) were added in the course of the synthesis in their protected form.

The peptide-resin was removed from the synthesizer and dried 1 hour in vacuo. Cleavage from the resin and removal of the protecting groups involved mixing a cooled solution of 10 mL trifluoroacetic acid (TFA), 0.75 g phenol, 0.25 mL 1,2-ethanediol, 0.5 mL thioanisole and 0.5 mL water with the chelator-peptide-resin for 2.5 hours at room temperature. The resin was removed by filtration and washed with 3 ml

| ROI Ratio of Inflamed v. Control | | | ROI Ratio of Infected v. Control | | |
|---|---|---|---|---|---|
| | Expt #1 n = 4 | Expt #2 n = 4 | | Expt #1 n = 4 | Expt #2 n = 4 |
| | Zymosan | | | E. coli | |
| 30 min | 1.98 ± 0.35 | 2.59 ± 0.14 | 30 min | 2.75 ± 0.23 | 2.72 ± 0.29 |
| 1 h | 1.56 ± 0.19 | 2.00 ± 0.13 | 1 h | 3.46 ± 0.39 | 2.47 ± 0.13 |
| 2 h | 1.90 ± 0.29 | 1.78 ± 0.21 | 2 h | 3.47 ± 0.27 | 1.76 ± 0.06 |
| 3 h | 1.23 ± 0.12 | 1.53 ± 0.25 | 3 h | 2.93 ± 0.56 | 2.23 ± 0.44 |
| 4 h | 1.86 ± 0.16 | | 4 h | 3.47 ± 0.13 | |
| 18 h | 0.99 ± 0.08 | | 18 h | 2.07 ± 0.33 | |
| | Carrageenan | | | S. aureus | |
| 30 min | | 2.41 ± 0.08 | 30 min | 3.03 ± 0.21 | 4.65 ± 0.23 |
| 1 h | | 1.84 ± 0.31 | 1 h | 2.80 ± 0.52 | 4.37 ± 0.39 |
| 2 h | | 2.05 ± 0.41 | 2 h | 2.87 ± 0.42 | 2.62 ± 0.31 |
| 3 h | | 1.38 ± 0.18 | 3 h | 2.04 ± 0.56 | 2.39 ± 0.34 |
| 4 h | | | 4 h | 2.57 ± 0.29 | |
| | | | 18 h | 1.41 ± 0.07 | |
| | | | | C. albicans | |
| | | | 30 min | 2.73 ± 0.14 | |
| | | | 1 h | 3.24 ± 0.39 | |
| | | | 2 h | 3.21 ± 0.35 | |
| | | | 3 h | 2.25 ± 0.49 | |
| | | | 4 h | 2.73 ± 0.36 | |
| | | | 18 h | 1.77 ± 0.12 | |

In order to determine the specificity of the peptide of FIG. 1 to image a site of infection v. a site of inflammation, a ratio of TFA to obtain 8 ml of a clear yellow solution. This solution was slowly dropped into 35 ml of tert-butyl methyl ether at 0° C. in a 50 ml conical polypropylene centrifuge tube forming a colourless precipitate.

The precipitate was centrifuged at 4500 rpm at −5° C. for 15 minutes (Sorvall RT 6000, Dupont), decanted and washed twice with t-butyl methyl ether. The precipitate was then dried under vacuum and then dissolved in water (2 ml), frozen at −78° C. (acetone-dry ice) and lyophilized over 20 hours to yield the crude peptide (530 mg). The crude peptide (24 mg) was dissolved in water (4 mL), filtered through a 0.45 µm syringe filter (Gelman Acrodisc LC PVDF), and purified by reversed-phase HPLC (Beckman System Gold) with a C18 column (Waters RCM 8×10) using 0.1% TFA in water as buffer A and 0.1% TFA in acetonitrile as buffer B. The column was equilibrated with 50:50 buffer A:buffer B for 10 min. and the peptide was eluted in 25 minutes using a linear gradient to 100% buffer B at 2 ml/min. Fractions were reanalysed on the HPLC and pooled according to matching profiles. The pure fractions were frozen at −78° C. (acetone-dry ice) and lyophilized over 20 hours to yield a pure peptide as a colourless powder (12 mg).

This peptide conjugate was labelled with $^{99m}$Tc in the manner described above in Example 2.

EXAMPLE 6

Binding Studies with a Synthetic Conjugate

This experiment was conducted as set out in detail in Example 3 using the synthetic conjugate of FIG. 2, and the results obtained are tabulated below:

| Time Elapsed | S. aureus | E. coli | C. albicans | HL60 |
| --- | --- | --- | --- | --- |
| | Experiment #1 | | | |
| 00:00 | 27.0% | 22.3% | 28.3% | |
| 00:30 | 36.2% | 21.0% | 9.1% | |
| 01:00 | 31.5% | 9.6% | 16.0% | |
| 02:00 | 39.8% | 20.7% | 8.0% | |
| 04:00 | 28.5% | 20.8% | 21.8% | |
| | Experiment #2 | | | |
| 00:00 | 18.6% | 6.1% | | 32.4% |
| 00:30 | 50.4% | 13.7% | | 43.1% |
| 01:00 | 51.1% | 16.4% | | 52.0% |
| 02:00 | 47.7% | 18.9% | | 52.8% |
| 04:00 | 39.9% | 20.8% | | 67.0% |
| | Experiment #3 | | | |
| 00:00 | 21.8% | 0.0% | 10.7% | 0.0% |
| 00:30 | 37.7% | 13.7% | 1.6% | 4.4% |
| 01:00 | 50.0% | 17.0% | 10.7% | 0.0% |
| 02:00 | 44.0% | 15.9% | 6.5% | 26.5% |
| 04:00 | 34.0% | 14.3% | 4.5% | 28.0% |

The results indicate binding of the synthetic conjugate of FIG. 2 to both microorganisms and tumour cells.

EXAMPLE 7

Imaging with a Synthetic Conjugate

This experiment was conducted as set out in detail in Example 4 using the synthetic conjugate of FIG. 2, and the results obtained are tabulated below:

| ROI Ratio of Inflamed v. Control | | ROI Ratio of Infected v. Control | |
| --- | --- | --- | --- |
| Zymosan | | E. coli | |
| 30 min | 2.52 ± 0.19 | 30 min | 2.16 ± 0.03 |
| 1 h | 2.04 ± 0.19 | 1 h | 1.98 ± 0.24 |
| 2 h | 2.07 ± 0.26 | 2 h | 1.88 ± 0.15 |
| 3 h | 1.86 ± 0.18 | 3 h | 1.69 ± 0.28 |
| 4 h | 2.26 ± 0.24 | 4 h | |
| 18 h | 1.54 ± 0.09 | | |
| Carrageenan | | S. aureus | |
| 30 min | 1.90 ± 0.34 | 30 min | 2.76 ± 0.28 |
| 1 h | 1.84 ± 0.28 | 1 h | 2.14 ± 0.37 |
| 2 h | 1.83 ± 0.32 | 2 h | 1.77 ± 0.17 |
| 3 h | 1.40 ± 0.18 | 3 h | 1.41 ± 0.11 |
| 4 h | | 4 h | 1.74 ± 0.07 |
| | | 21 h | 1.61 ± 0.06 |

The ratios of the ROI ratios obtained by imaging the inflamed sites v. the infected sites were calculated in order to determine the specificity of the synthetic conjugate to image sites of infection. These ratios were calculated for each experiment at the 1 hour readings. The ratio between the ROIs at the E. coli infected sites vs. inflamed sites with zymosan and carrageenan were 0.97 and 1.08, respectively. For S. aureus infected sites, the ratios were 1.05 and 1.16 based on a comparison with zymosan and carrageenan inflamed sites.

The results in this case indicate, despite the in vitro binding data obtained (and provided in Example 6 above), that the labelled synthetic peptide conjugate of FIG. 2 does not efficiently distinguish between sites of infection and sites of inflammation in vivo. These results were unexpected particularly due to the fact that the peptide exhibited specific binding to a number of infectious agents in vivo. In order to understand the in vivo results obtained, computer-simulated models of the cell-associating component of the synthetic peptide of FIG. 2 and its conjugated form were compared to similar models of the cell-associating component of the peptide of FIG. 1 and its conjugated form, particularly since the conjugate of FIG. 1 was found to image specifically sites of infection.

Figure 3A:
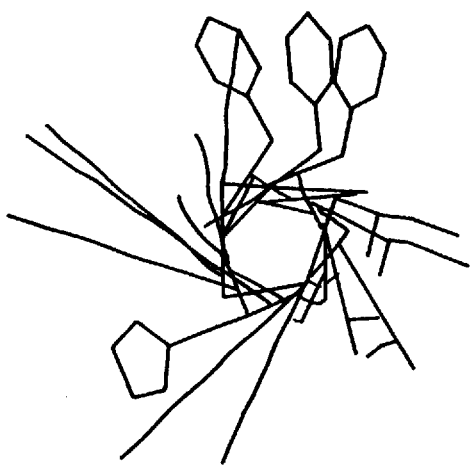
FIG. 3 illustrates, by molecular model, the conformation of the cell-associating component of the peptide of FIG. 1 (A) and its conjugated form (B)
Figure 3B:
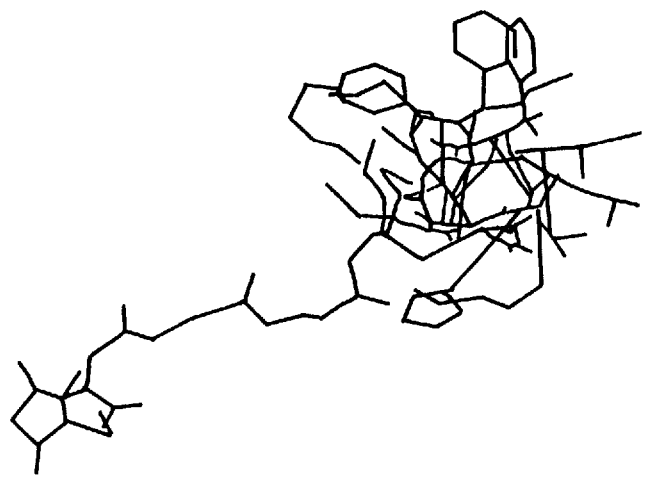

FIG. 3 illustrates the cell-associating component of FIG. 1 and the conjugate prepared therefrom which was used in the in vitro and in vivo binding studies. The cell-associating component possesses a distinct α-helical conformation, and the conjugate prepared therefrom essentially retains this α-helical conformation thereby allowing the conjugate to retain target recognition and binding activity, as illustrated by both in vitro and in vivo binding studies.

Figure 4A:
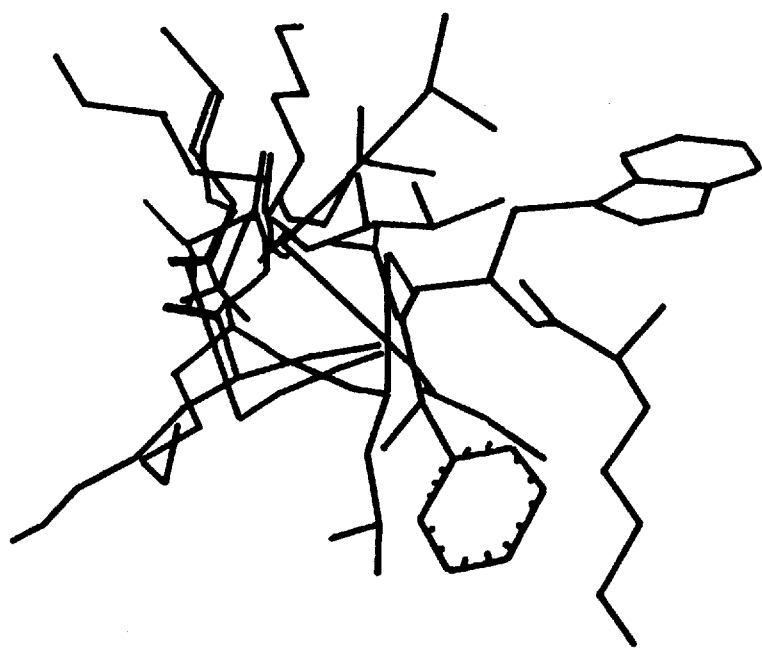
FIG. 4 illustrates, by molecular model, the conformation of the cell-associating component of the peptide of FIG. 2 (A) and its conjugated form (B).
Figure 4B:
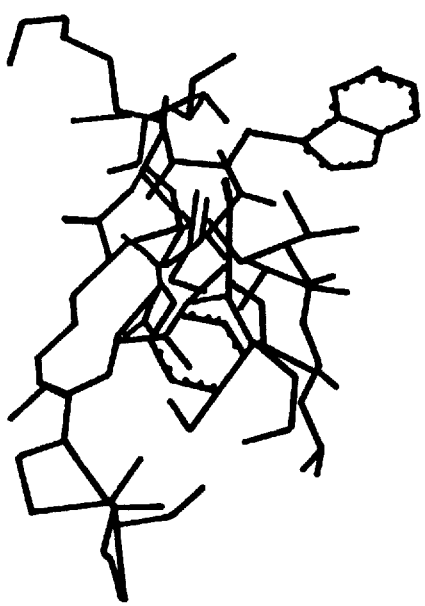

FIG. 4 illustrates the cell-associating component of FIG. 2 and the conjugate prepared therefrom used in vitro and in vivo binding studies. In this case, the α-helical conformation of the cell-associating component, which is weaker than that of the peptide of FIG. 1, is not retained on formation of the conjugate. Thus, although some specific target binding occurred in vitro, the conjugate's loss of conformation resulted in loss of specific binding activity in vivo. Thus, these results establish the significance attached to the retention of the native cell-associating conformation of a peptide in its conjugated form for its effective use in specifically imaging sites of infection.

We claim:

1. A non-receptor mediated cell-associating compound coupled to a detectable label for use in imaging a target site in a mammal, wherein said compound essentially retains its native conformation on coupling to said label.

2. A compound as defined in claim 1, which is a peptide.

3. A compound as defined in claim 1, which is a microorganism-binding compound.

4. A compound as defined in claim 1, wherein said label is linked to said compound via a chelator.

5. A compound as defined in claim 4, wherein said label is technetium-99m, or a nitride or oxide thereof.

6. A non-receptor mediated cell-associating compound coupled to a detectable label, wherein said compound is selected from the group consisting of magainin peptides, and functionally equivalent analogues thereof.

7. A compound as defined in claim 6, which is magainin-1.

8. A compound as defined in claim 6, wherein said label is linked to said compound via a chelator.

9. A compound as defined in claim 8, wherein said chelator is linked to said compound via a linker.

10. A compound as defined in claim 9, wherein said linker is a peptide.

11. A diagnostic composition comprising a compound as defined in claim 1, in admixture with a pharmaceutically acceptable aqueous carrier.

12. A diagnostic composition comprising a compound as defined in claim 6, in admixture with a pharmaceutically acceptable aqueous carrier.

13. A method for imaging a target site in a mammal, said method comprising the steps of administering to said mammal a composition as defined in claim 12, and detecting the site of accumulated radioactivity in said mammal.

14. A method as defined in claim 13, wherein said composition is administered at a dosage in the range of 1–100 mCi per 70 kg.

15. A method as defined in claim 13, wherein said target site is a site of infection.

16. A method as defined in claim 13, wherein said target site is a tumour.

17. A kit comprising:
- a non-receptor mediated cell-associating compound linked to a chelator to form a conjugate;
- a reducing agent;
- a buffering agent; and
- a transchelating agent.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note= "A dimethyl group is linked at position 1"

( i x ) FEATURE:
( A ) NAME/KEY: Modified-site
( B ) LOCATION: 3
( D ) OTHER INFORMATION: /note= "An Acm group is linked at position 3"

( i x ) FEATURE:
( A ) NAME/KEY: Modified-site
( B ) LOCATION: 4..6
( D ) OTHER INFORMATION: /note= "The alanine residues at positions 4, 5 and 6 are beta-alanine residues"

( x i ) SEQUENCE DESCRIPTION: SEQ ID NO:1:

Gly Ser Cys Ala Ala Ala Gly Ile Gly Lys Phe Leu His Ser Ala Gly
1               5                   10                  15

Lys Phe Gly Lys Ala Phe Val Gly Glu Ile Met Lys Ser
            20                  25

( 2 ) INFORMATION FOR SEQ ID NO:2:

( i ) SEQUENCE CHARACTERISTICS:
( A ) LENGTH: 19 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note= "A dimethyl group is linked at position 1"

( i x ) FEATURE:
( A ) NAME/KEY: Modified-site
( B ) LOCATION: 3
( D ) OTHER INFORMATION: /note= "An Acm group is linked at position 3"

( x i ) SEQUENCE DESCRIPTION: SEQ ID NO:2:

Gly Ser Cys Gly Lys Trp Lys Leu Phe Lys Lys Ile Gly Ala Val Leu
1               5                   10                  15

Lys Val Leu